(12) United States Patent
Mizukami et al.

(10) Patent No.: US 6,359,163 B2
(45) Date of Patent: Mar. 19, 2002

(54) PROCESS FOR PRODUCING DIALKYL CARBONATE

(75) Inventors: Masamichi Mizukami; Yoshihisa Arai; Hidefumi Harada, all of Tsukuba (JP)

(73) Assignee: Mitsubishi Gas Chemical Company Inc., Tokyo (JP)

( * ) Notice: Subject to any disclaimer, the term of this patent is extended or adjusted under 35 U.S.C. 154(b) by 0 days.

(21) Appl. No.: 09/877,044

(22) Filed: Jun. 11, 2001

(30) Foreign Application Priority Data

Jun. 12, 2000 (JP) ............................................ 12-175064

(51) Int. Cl.$^7$ ............................................... C07C 69/96
(52) U.S. Cl. ........................................................ 558/277
(58) Field of Search ........................................ 558/277

(56) References Cited

FOREIGN PATENT DOCUMENTS

| JP | 55-102543 | 8/1980 | ........... C07C/69/96 |
|----|-----------|--------|-----------------------|
| JP | 10-109960 | 4/1998 | ........... C07C/69/96 |
| JP | 11-60541  | 3/1999 | ........... C07C/69/96 |

*Primary Examiner*—T. A. Solola
*Assistant Examiner*—Joseph Murray
(74) *Attorney, Agent, or Firm*—Sughrue Mion, PLLC

(57) ABSTRACT

A process for producing a dialkyl carbonate which comprises performing reaction of allophanate represented by the following general formula (1) and an alkyl alcohol represented by the following general formula (2) as raw materials, thereby producing a dialkyl carbonate represented by the following general formula (3).

$$RO—CO—NH—CO—NH_2 \quad (1)$$

$$ROH \quad (2)$$

$$RO—CO—OR \quad (3)$$

wherein R is an alkyl group.

11 Claims, 1 Drawing Sheet

PROCESS FOR PRODUCING DIALKYL CARBONATE

BACKGROUND OF THE INVENTION

1) Field of the Invention

The present invention relates to a process for producing a dialkyl carbonate, and specifically, to a process for effective utilization of allophanate by-produced during reaction or at a purifying stage in the production of a dialkyl carbonate comprising reacting urea and alcohol. The dialkyl carbonate produced according the process of the present invention is useful as a raw material of diaryl carbonate.

2) Prior Art

Japanese Patent Kokai (Laid-open) No. 55-102542 describes a process for producing a dialkyl carbonate by reaction of urea and alcohol. Japanese Patent Kokai (Laid-open) Nos. 55-102543, 57-175147 and 57-26645 describe processes for producing a dialkyl carbonate by reaction of alkyl carbamate and alcohol and further Japanese Patent Kokai (Laid-open) Nos. 10-109960, 10-259163, 10-259166 and 11-60541 disclose improved processes thereof. However, in above-mentioned prior art gazettes, the production of a by-product and its component have been not known.

SUMMARY OF THE INVENTION

The inventors have found that a solid substance having an indistinct structure is produced in the production of a dialkyl carbonate from urea and alcohol and deposited on a condenser of a distillation column and pipes in its vicinity. When operation of the distillation column was performed without removing it, there caused problems that pipes were blockaded to prevent a flow of liquid and accurate flow rate was not indicated due to its deposition on a flow meter. Thus, it was necessary to remove the solid substance with a strainer or in a settling vessel. Further, the inventors analyzed the solid substance and found that it is allophanate. However, properties of allophanate were not known in detail. Therefore, any method except waste disposal of allophanate was not found. Since allophanate is by-produced from urea or alkyl carbamate of a raw material, waste disposal of allophanate to be by-produced caused lowering unit consumption of raw material.

From the above-mentioned viewpoints, an object of the present invention is to provide a process for effective utilization of allophanate by-produced and to eliminate an apparatus for removing allophanate by-produced and operation for removal thereof.

As a result of extensive studies to utilize effectively allophanate as a by-product which has been waste disposed hitherto, the inventors have found that allophanate can be used as a raw material instead of urea or together with urea in the production of a dialkyl carbonate and furthermore can be returned to a reactor for production of a dialkyl carbonate in the state of an alcohol solution or a slurry without performing separation, and have accomplished the present invention.

That is, the present invention provides a process for producing a dialkyl carbonate which comprises performing reaction of allophanate represented by the following general formula (1) and an alkyl alcohol represented by the following general formula (2) as raw materials, thereby producing a dialkyl carbonate represented by the following general formula (3).

$$RO-CO-NH-CO-NH_2 \qquad (1)$$

$$ROH \qquad (2)$$

$$RO-CO-OR \qquad (3)$$

wherein R is an alkyl group.

Further, the present invention provides a process for producing a dialkyl carbonate which comprises performing reaction of urea and/or an alkyl carbamate represented by the following general formula (4) and an alkyl alcohol represented the following general formula (2) as raw materials, thereby producing a dialkyl carbonate represented by the following general formula (3), wherein allophanate represented by the following general formula (1) to be produced as by-product is reused as one of raw materials.

$$RO-CO-NH-CO-NH_2 \qquad (1)$$

$$ROH \qquad (2)$$

$$RO-CO-OR \qquad (3)$$

$$RO-CO-NH_2 \qquad (4)$$

wherein R is an alkyl group.

DETAILED DESCRIPTION OF THE INVENTION

Figure 1:
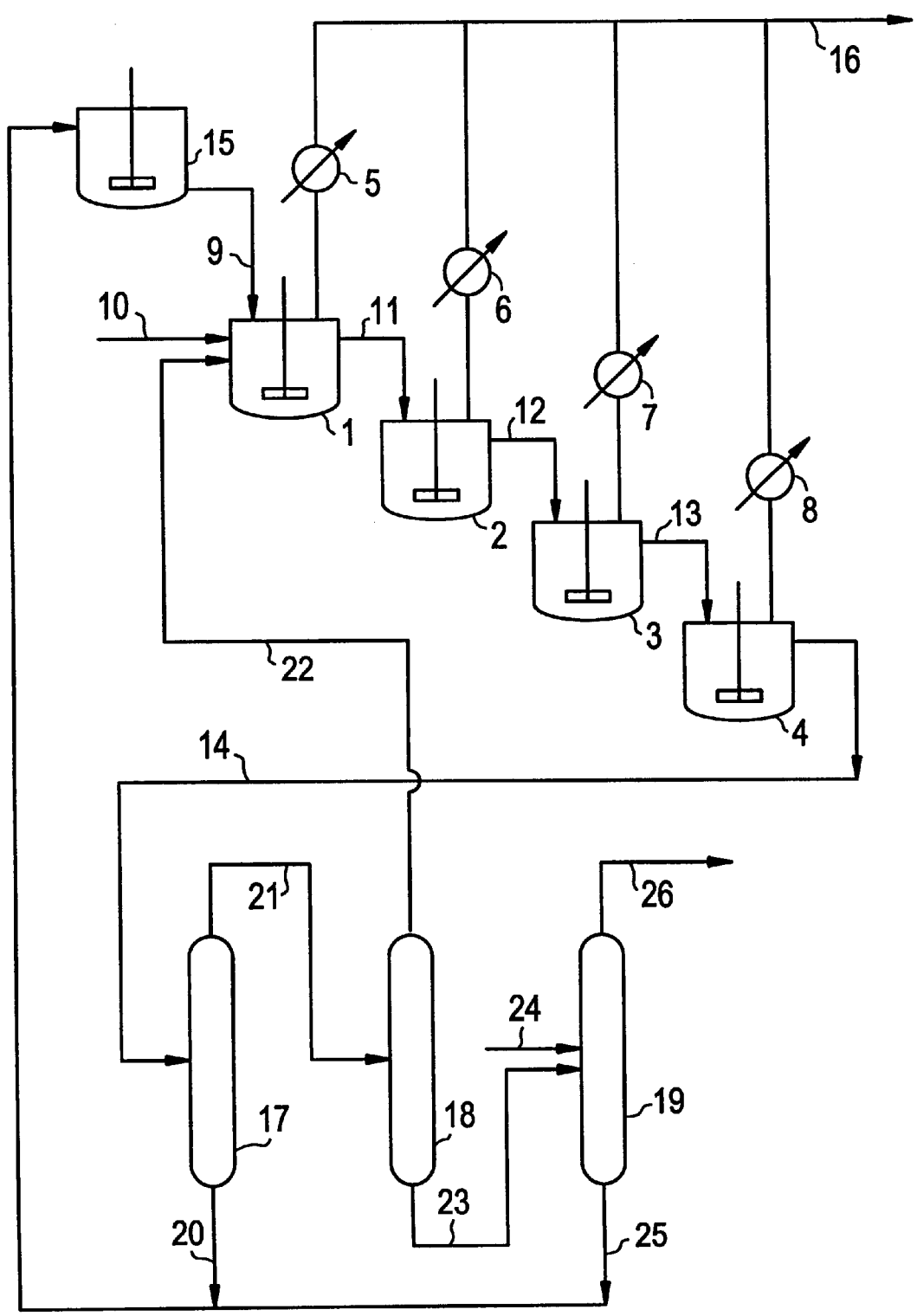
FIG. 1 is a flow sheet including apparatuses for continuous reaction and purification of the present invention.

The present invention will be described in detail below.

The alkyl alcohol to be used as a raw material for the production of a dialkyl carbonate is not limited. An alkyl alcohol having 3 to 6 carbon atoms (R in above-mentioned general formulas: an alkyl group having 3 to 6 carbon atoms) is preferable. Examples of the alkyl alcohol include propanol, butanol, pentanol, hexanol and isomers thereof.

As other raw material, allophanate can be used instead of urea. Although only allophanate can be used instead of urea, it is preferable to add allophanate obtained as a by-product to urea, alkyl carbamate or a mixture of urea and alkyl carbamate as raw materials.

The alkyl carbamate of the present invention is an intermediate of a dialkyl carbonate to be obtained in the reaction of urea and above-mentioned alkyl alcohol. Although it is possible also to advance the reaction until alkyl carbamate disappears, the reaction is stopped prior to its disappearance and then alkyl carbamate is recovered from the reaction liquid and can be also reused as a raw material.

Each proportion of urea, alkyl carbamate and allophanate is not limited. In the present invention, when only allophanate is used instead of urea as a raw material, a dialkyl carbonate represented by the general formula (3) is produced by reaction of allophanate represented by the general formula (1) and an alkyl alcohol represented by the general formula (2).

RO—CO—NH—CO—NH$_2$ (1)

ROH (2)

RO—CO—OR (3)

wherein R is an alkyl group and preferably an alkyl group having 3 to 6 carbon atoms.

Further, when allophanate is used as one of raw materials, a dialkyl carbonate represented by the general formula (3) is produced by reaction of urea and/or alkyl carbamate represented by the general formula (4), allophanate represented by the general formula (1) of a by-product and an alkyl alcohol represented by the general formula (2).

RO—CO—NH—CO—NH$_2$ (1)

ROH (2)

RO—CO—OR (3)

RO—CO—NH$_2$ (4)

wherein R is an alkyl group and preferably an alkyl group having 3 to 6 carbon atoms.

These raw materials are mixed. The reaction in a mixture thus obtained is performed with heating in the presence of a catalyst. In order to advance readily the reaction, it is necessary to exhaust ammonia produced by the reaction outside the reaction system. Therefore, it is preferable that the reactor is equipped with a reflux condenser and the reaction is performed in the state in which the reaction liquid is refluxed. Alkyl carbamate is produced at the initial stage of the reaction from allophanate and urea. When the reaction temperature is too high at this stage, side reaction occurs. It is preferable that the reaction temperature at the initial stage of the reaction is 100 to 200° C. and the reaction temperature at the stage to produce a dialkyl carbonate from alkyl carbamate is 160 to 260° C.

It is preferable that the reaction is performed in a high boiling point solvent having a boiling point of 180° C. or above. Although it is necessary to apply a pressure in order to maintain preferable reaction temperature without using a high boiling point solvent, the reaction can be performed under about atmospheric pressure by using a high boiling point solvent. Examples of preferable high boiling point solvent include hydrocarbons and ethers. Although the hydrocarbons may be aliphatic unsaturated hydrocarbons, saturated hydrocarbons or aromatic hydrocarbons having high stability are preferable. Ethers may be aromatic ethers, aliphatic ethers or aromatic aliphatic ethers.

Examples of preferable hydrocarbon solvent include undecane, dodecane, tridecane, tetradecane, pentadecane, hexadecane, heptadecane, octadecane, nonadecane, eicosane, tetramethylpentadecane, dicyclohexyl, hexylbenzene, cyclohexylbenzene, heptylbenzene, octylbenzene, nonylbenzene, decylbenzene, undecylbenzene, diisopropylbenzene, triisopropylbenzene, pentamethylbenzene, methylnaphthalene, diphenylmethane, ethylbiphenyl, bibenzyl and isomers thereof.

Examples of preferable ether solvent include dihexyl ether, dioctyl ether, cyclododencyl methyl ether, diethyleneglycol dimethyl ether, diethyleneglycol dibutyl ether, triethyleneglycol dimethyl ether, tetraethyleneglycol dimethyl ether, butyl phenyl ether, benzyl phenyl ether, dibenzyl ether, diphenyl ether, ditolyl ether and isomers thereof.

It is preferable that the amount of high boiling point solvent is about 0.1 to 10 mol per 1 mol of sum total of urea, alkyl carbamate and allophanate as the raw materials. It is preferable that the amount of alkyl alcohol is about 0.5 to 10 mol per 1 mol of sum total of urea, alkyl carbamate and allophanate as the raw materials.

As the catalyst for the reaction, the catalyst described in Japanese Patent Kokai (Laid-open) Nos. 55-102542, 55-102543, 57-26645 and 57-175147 can be used. Among them, particularly, an oxide, a hydroxide, a halogenide, an inorganic salt, an organic salt, an alkoxide, an alkyl-substituted oxide or an alkylalkoxide of at least one metal selected from the group consisting of zinc, lead, copper, tin, titanium, gallium and indium exhibits high activity for the reaction.

The reaction can be performed in a batch process or in a continuous process. In a batch process, it is preferable that total amount of alkyl alcohol is not added at the starting time of the reaction, but gradually added with progress of the reaction. In a continuous process, it is preferable that the reaction is performed in a cascade process with plural reactors. It is preferable that the number of the reactor is 3 to 5. Alkyl alcohol can be fed to each reactor.

After the completion of the reaction, the intended dialkyl carbonate can be obtained by separating by distillation from the reaction liquid. It is possible to separate both the catalyst and the high boiling point solvent contained in the reaction liquid as high boiling matter in distillation and the alkyl alcohol as low boiling matter in distillation. Allophanate is separated together with alkyl alcohol as low boiling matter since it is a substance having a sublimation property. Although the liquid removed both low boiling matters and high boiling matters can be used as dialkyl carbonate, if necessary, further distillation purification may be performed. In this case, as described in Japanese Patent Kokai (Laid-open) No. 2000-1461, it is possible also to promote the separation by adding a third substance.

Allophanate contained in alkyl alcohol can be separated by filtration since it is deposited by cooling. In order to perform efficiently the separation, it is preferable that a settling vessel is equipped and allophanate is deposited on its bottom section and then filtered. Allophanate thus separated is not only used alone as the raw material, but used together with urea and/or alkyl carbamate as one of the raw materials.

Industrially, it is preferable that an alkyl alcohol solution of allophanate obtained by distillation or a slurry thereof is used as the raw material for the reaction since the efficiency is low when allophanate is filtered. Total amount of alcohol separated by distillation may be returned to the reactor since the alkyl alcohol is unreacted and its total amount is smaller than an amount to be required for the reaction. Therefore, the reaction can be performed again by adding urea and/or alkyl carbamate and alkyl alcohol to the liquid.

PREFERRED EMBODIMENT OF THE INVENTION

The present invention will be described in more detail below, referring to Examples, which are not intended to limit the scope of the present invention.

The word "butyl" described in Examples means "n-butyl".

EXAMPLE 1

A reactor equipped with a separable flask of capacity 500 ml with a baffle plate connected an Allihn cooler and a stirrer of fan turbine blade was used. Hot water of 60° C. was passed through the cooler. 25.00 g (156 mmol) of butyl allophanate, 5.70 g (76.9 mmol) of butanol, 2.89 g (11.6 mmol) of dibutyl tin oxide and 214.70 g (1.26 mol) of diphenyl ether were charged to the reactor and reacted for 4 hours with stirring while heating in an oil bath. It was considered that the time when the temperature of reaction liquid reached to 130° C. was reaction start time. Then, the temperature was adjusted so as to maintain 180° C. after one hour of the reaction starting, 200° C. after 2 hours and 205 to 210° C. after 4 hours. The oil bath temperature was gradually elevated from 160° C. at the time of the reaction starting to 235° C. at the time of the reaction completion. Butanol was added during the reaction so as not to elevate the reaction temperature to excess. Total amount of butanol used as the raw material was 33.37 g (450 mmol). After the completion of the reaction, the yield of dibutyl carbonate was 36.24 g (208 mmol). The yield of dibutyl carbonate based on butyl allophanate was 66.7%.

EXAMPLE 2

The reaction was performed in the same manner as in Example 1 except that 12.50 g (78.0 mmol) of butyl allophanate and 9.37 g (156 mmol) of urea were used instead of 25.00 g of butyl allophanate as the raw material and charge of butanol was changed from 5.70 g to 17.38 g (234.5 mmol). Total amount of butanol used as the raw material became 38.54 g (520 mmol). After the completion of the reaction, the yield of dibutyl carbonate was 33.80 g (194 mmol) and the yield of dibutyl carbonate based on total amount of butyl allophanate and urea was 62.2%.

EXAMPLE 3

The reaction and purification were performed, as shown in FIG. 1, using four stage continuous reactors and three distillation columns. In each reactors 1, 2, 3 and 4, a vessel of capacity 350 L equipped with a baffle and a stirrer was used. 0.037 mol of dibutyl tin oxide and 4 mol of diphenyl ether per 1 mol of urea were added to preliminary mixing vessel 15 to disperse uniformly and then continuously introduced to reactor 1 via conduit pipe 9. The introduction rate was adjusted so as to maintain 100 kg/hr. Heating was performed by passing a heated medium of 230° C. through a coil to each reactor. The temperature in each reactor was adjusted so as to maintain 170° C. in reactor 1, 180° C. in reactor 2, 190° C. in reactor 3 and 200° C. in reactor 4. Butanol was introduced via conduit pipe 10 so as to maintain the reaction temperature to a prescribed temperature. The amount of butanol to be introduced via conduit pipe 10 during steady operation became 10 kg/hr. Hot water of 60° C. was passed through reflux condensers 5, 6, 7 and 8. The reaction liquid was withdrawn via reaction liquid withdrawing pipes 11, 12, 13 and 14 connected to each reactor so as to maintain the liquid amount in each reactor to 230 L. Ammonia generated from each reactor was separated from butanol through reflux condensers 5, 6, 7 and 8 and then exhausted via conduit pipe 16.

The reaction liquid was introduced to distillation column 17 via conduit pipe 14. The introduction rate was 108 kg/hr. Distillation column 17 was adjusted so as to maintain column top pressure of 2.7 kPa, column top temperature of 102° C. and column bottom temperature of 145°. The column bottom liquid, which was a mixture of the catalyst and diphenyl ether, was returned to preliminary mixing vessel 15 via conduit pipe 20 to reuse.

The mixture of butanol, dibutyl carbonate, butyl carbamate, diphenyl ether and butyl allophanate obtained from the column top section was introduced to distillation column 18 via conduit pipe 21. Distillation column 18 was adjusted so as to maintain column top pressure of 13.3 kPa, column top temperature of 67° C. and column bottom temperature of 140° C. Butanol and butyl allophanate were obtained from the column top section and introduced to reactor 1 via conduit pipe 22 as a slurry liquid of butyl allophanate. The introduction amount was butanol 3 kg/hr and butyl allophanate 150 g/hr.

The mixture of dibutyl carbonate, butyl carbamate and diphenyl ether was introduced to distillation column 19 via conduit pipe 23. In order to ensure efficient separation of dibutyl carbonate and butyl carbamate, phenol was introduced to distillation column 19 via conduit pipe 24. Distillation column 19 was adjusted so as to maintain column top pressure of 2.7 kPa, column top temperature of 91° C. and column bottom temperature of 125° C. A mixture of dibutyl carbonate and phenol was obtained from the column top section via conduit pipe 26. A mixture of butyl carbamate and diphenyl ether obtained from the column bottom section was returned to preliminary mixing vessel 15 via conduit pipe 25 to reuse.

After introduction of butyl carbamate to preliminary mixing vessel 15 via conduit pipe 25 was started, the feed amount of urea was adjusted so as to maintain 1 mol of sum total of butyl carbamate and urea per 4 mol of diphenyl ether.

The apparatuses were continuously operated for 80 hours. Steady state was reached after 30 hours of operation starting. The feed rate of urea in a steady state was 72.5 mol/hr, whereas the production rate of dibutyl carbonate to be obtained via reaction liquid withdrawing pipe 14 was 72.2 mol/hr (99.6 mol % to fed urea). The yield of dibutyl carbonate based on urea was increased more by 2.6% than in Comparative Example 1 where butyl allophanate was not returned to reactor 1.

Comparative Example 1

The operation was performed for 80 hours in the same apparatuses and procedure as in Example 1 except that butyl allophanate was cooled to 5° C. to deposit in a settling vessel equipped in a lower portion of condenser of distillation column 18 and only butanol was returned to reactor 1 via conduit pipe 22. But, in order to remove butyl allophanate, procedures to withdraw butyl allophanate from the settling vessel every one hour and filter out it from butanol became necessary. The feed rate of urea in a steady state was 73.3 mol/hr, whereas the production rate of dibutyl carbonate to be obtained via reaction liquid withdrawing pipe 14 was 71.1 mol/hr (97.0 mol % to fed urea).

The present invention provides a novel process for producing dialkyl carbonate. Further, according to the process of the present invention, unit consumption of raw material is enhanced and a step for separation removal of allophanate can be eliminated in a process for production of dialkyl carbonate.

What is claimed is:

1. A process for producing a dialkyl carbonate which comprises performing reaction of allophanate represented by the following general formula (1) and an alkyl alcohol represented by the following general formula (2) as raw materials, thereby producing a dialkyl carbonate represented by the following general formula (3).

$$RO\text{---}CO\text{---}NH\text{---}CO\text{---}NH_2 \quad (1)$$

$$ROH \quad (2)$$

$$RO\text{---}CO\text{---}OR \quad (3)$$

wherein R is an alkyl group.

2. The process according to claim 1, wherein R is an alkyl group having 3 to 6 carbon atoms.

3. The process according to claim 1, wherein said reaction is performed in the presence of a catalyst.

4. The process according to claim 3, wherein said catalyst is an oxide, a hydroxide, a halogenide, an inorganic salt, an organic acid salt, an alkoxide, an alkyl-substituted oxide or an alkylalkoxide of at least one metal selected from the group consisting of zinc, lead, copper, tin, titanium, gallium and indium.

5. The process according to claim 1, wherein said reaction is performed at a temperature of 100 to 260° C.

6. The process according to claim 1, wherein said reaction is performed in a high boiling point solvent having a boiling point of 180° C. or above.

7. A process for producing a dialkyl carbonate which comprises performing reaction of urea and/or an alkyl carbamate represented by the following general formula (4) and an alkyl alcohol represented the following general formula (2) as raw materials, thereby producing a dialkyl carbonate represented by the following general formula (3), wherein allophanate represented by the following general formula (1) to be produced as by-product is reused as one of raw materials.

$$RO\text{---}CO\text{---}NH\text{---}CO\text{---}NH_2 \quad (1)$$

$$ROH \quad (2)$$

$$RO\text{---}CO\text{---}OR \quad (3)$$

$$RO\text{---}CO\text{---}NH_2 \quad (4)$$

wherein R is an alkyl group.

8. The process according to claim 7, wherein R is an alkyl group having 3 to 6 carbon atoms.

9. The process according to claim 7, wherein said allophanate is separated by filtration.

10. The process according to claim 7, wherein said allophanate is separated and then fed to a reactor together with urea as raw material.

11. The process according to claim 7, wherein said allophanate is fed to a reactor as a slurry or a solution of alkyl alcohol represented by the general formula (2) without performing separation.

* * * * *